Figure 4:
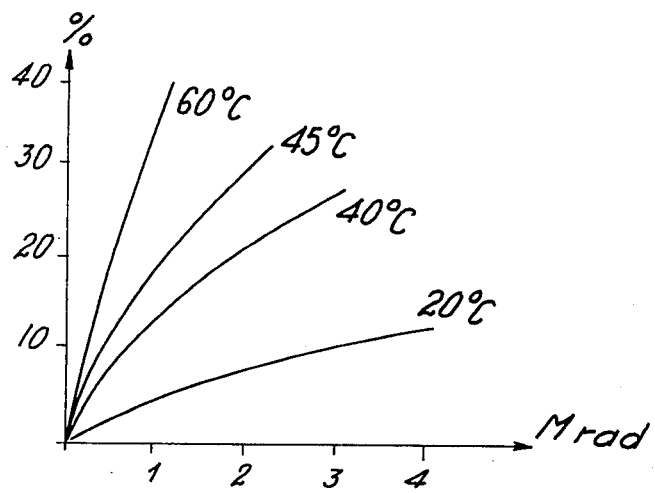

United States Patent [19]
Cournut

[11] 3,934,580
[45] Jan. 27, 1976

[54] CHEMICALLY ACTING INTRA-UTERINE DEVICE

[75] Inventor: Rene Cournut, Bordeaux-Cauderan, France

[73] Assignee: Apamed Anstalt, Vaduz, Liechtenstein

[22] Filed: Nov. 11, 1974

[21] Appl. No.: 522,966

[30] Foreign Application Priority Data
Nov. 9, 1973 France .......................... 73.40003

[52] U.S. Cl................................. 128/130; 128/260
[51] Int. Cl.² ..................... A61F 5/46; A61M 31/00
[58] Field of Search .......... 128/130, 260, 270, 294; 424/19, 20, 21

[56] References Cited
UNITED STATES PATENTS

| | | | |
|---|---|---|---|
| 3,633,574 | 1/1972 | Lerner | 128/130 |
| 3,659,596 | 5/1972 | Robinson | 128/130 |
| 3,785,376 | 1/1974 | Kitrilakis | 128/130 |
| 3,786,808 | 1/1974 | Lerner | 128/130 |
| 3,845,761 | 11/1974 | Zaffaroni | 128/130 |

*Primary Examiner*—Aldrich F. Medbery
*Attorney, Agent, or Firm*—Sughrue, Rothwell, Mion, Zinn & Macpeak

[57] ABSTRACT

The invention is directed to an active intrauterine device comprising a hydrophobic substrate of high mechanical resiliency, wherein the substrate including within the volume thereof inclusions of polymerizied hydrophilic substances grafted on the hydrophobic substrate and cross-linked, and in which water-soluble chemical agents have been stored previously, these agents being adapted to perfuse through the hydrophobic substrate when the latter is placed in an aqueous medium.

14 Claims, 7 Drawing Figures

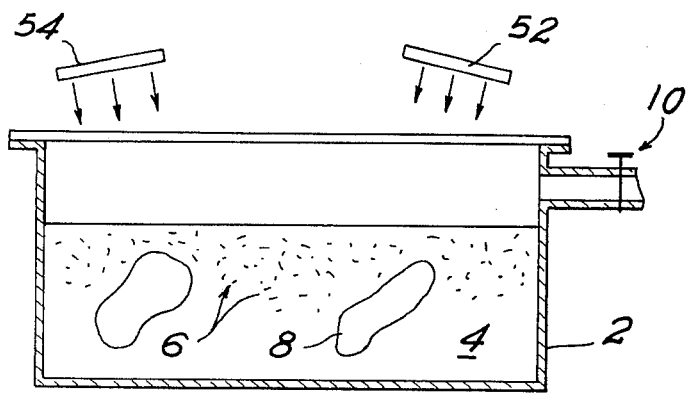
FIG. 1
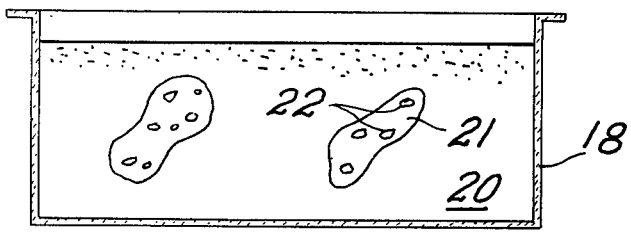
FIG. 2
FIG. 3
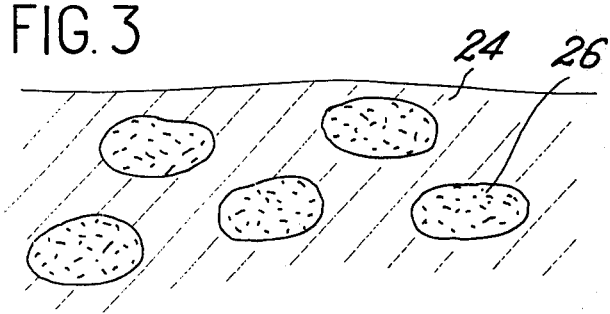

CHEMICALLY ACTING INTRA-UTERINE DEVICE

The present invention relates to an intra-uterine device comprising a hydrophobic substrate comprising hydrophilic inclusions which, contingently, contain active substances.

The basis invention can be utilized in particular but by no means exclusively, in the manufacture of a chemically acting intrauterine device for contraception. The term "contraception" generally covers all the methods for transiently and reversibly rendering sexual intercourse non fecundative. The standards of reference for appraising contraceptive methods are efficiency, innocuity, reversibility and acceptability.

It is well-known that since the remotest antiquity intra-uterine contraception had been a employed. With respect to animals, for example, the Arabs made it a practice for centuries to insert a stone into their she-camel's uterus.

In 1909, Richter made the first genuine attempt to apply intra-uterine contraception to human clinic. The intr-uterine device, as described by Richter, consisted of a silkthread loop knotted, in rather slap-dash fashion, by means of a brass-wire fastener, and was inserted into the uterus by means of a metal probe. Between 1909 and 1929 there appeared on the market intra-uterine contraceptive devices, usually consisting of an intra-uterine ring connected to an intra-cervical rod carrying at one end thereof a button adapted to cover the outer orifice of the uterus entrance.

Such a device very often gave rise to an ascending infection which tended to propagate from the vagina up to its appendages.

In 1929, Grafenberg invented an intra-uterina device in the form of silk-thread ring, which after 1930 was replaced by a silver thread, which was more easily sensed by X-rays. The failure-rate was 3% (as measured in women-years) and the rejection-rate was 5%.

In the 1960 the use of intra-uterine contraceptive devices of plastics combined with use of anti-biotics made the intra-uterine contraceptive method both less shock-promoting and less dangerous.

Attempts were made at finding intra-uterine devices having shapes best suited to the uterine cavity. Successive improvements led to shapes such as those of articles available on the market under the trade-names DALKON SHIELD or OM-GA, which were prone to cover a large portion of the endometrium surface. Again, attempts were made to obtain a toxic effect on blastocyst through a supply of metal ions, such as copper ions. Such active intra-uterine devices contain metals for increasing the local effects of the intra-uterine devices, contrary to inert intra-uterine devices of polyethylene or of inactive metals. The main advantage of such active intra-uterine devices lie in reducing the failure-percentage of about 2% of mechanically-acting intra-uterine inert devices.

Unfortunately, the conventional copper intra-uterine devices, in the form of a thread, sometimes give rise to uterus perforations. Moreover, other types of intra-uterine devices made of a resilient material on which is deposited copper for instance, lose their resiliency once thus covered, and there is risk that the copper film will scale off. It has proved necessary that the contraceptive-loaded intra-uterine device keep its memory-effect, namely a fair resiliency corresponding to an appropriate mechanical elasticity. In addition, it is advisable that copper-salts or any other contraceptive or treatment agents should be discharged into the uterus by the intra-uterine device at a pretty low constant speed. While the intra-uterine device is of limited size, it must at the same time keep in store a sufficient amount of contraceptive substances for remaining within the uterus for a long time before being replaced.

On the other hand, it is preferable to introduce into the uterus, in addition to the intra-uterine device, substances serving to better acclimatize the intra-uterine device within the uterus.

With regard to the above remark, the improvement of an intra-uterine device makes it necessary to meet the following requirements:

the shape, size and area of the device should comply with the uterine cavity morphology;

it is necessary to add a product adapted to be expelled within a few months, in order to thwart the uterus tendency to expel the intra-uterine device and with a view to avoiding the necessity of withdrawing the device because of bleeding or to preventing the occurrence of side-effects following insertion;

it is necessary to add a contraceptive or treatment product. In the case of a contraceptive product, the active life of the intra-uterine device should exceed one year.

Accordingly, the object of the invention is an active intra-uterine device comprising a hydrophobic substrate of high mechanical resiliency, wherein the substrate comprises, within the volume thereof, inclusions of polymerized hydrophilic substances, grafted on the hydrophobic substrate and cross-linked, in which water-soluble chemical agents have been stored previously, these agents being adapted to perfuse through said hydrophobic substrate when the latter is placed in an aqueous medium.

Taking account of the chemical agents included, the applications of the intra-uterine device are as follows:

contraception treatment metrites and endometrites by means of antibiotics.

treatment of endometrium cancer through hormones (high dose progestational substances)

treatment of sterility, by inserting a controlled-pH buffer-product into the hydrophilic inclusions treatment of menaupose through progesterones treatment of synechhiae (purely mechanical action aiming at preventing the uterus walls from touching each other).

all other treatments of women's genital organs (fibromas, cysts, etc)

treatment of genital tuberculosis by means of cortisone therapeutical abortion through prostaglandine. With an inert intra-uterine device (I.U.D.), the lower the pregnancy-rate, the higher the abandonment rate on medical grounds. Thus, an increasing efficiency gives rise to increasing side-effects.

With an active I.U.D., one can have at one's disposal a shape, a size and an area which, though not ensuring an optimum efficiency, however substantically cancel the sideeffects (traumatizing effects, tendency to expel the device) consisting in blood-losses and aches, since the shape, size and area are directly connected to mechanical tolerance. The desired efficiency increase is bound to the active chemical agent released.

The intra-uterine device, or I.U.D., according to the invention has numerous advantages: the risk of a perforated uterus are minimized (better acceptability) since the contact between the I.U.D. and the uterus wall is both resilient and soft.

The I.U.D. keeps a good mechanical resiliency once metal-salts or other pharmaceutical substances have been introduced.

Moreover, the grafting of hydrophilic monomers ensures a very good anchoring of the hydrophilic products onto the substrate, usually through co-valent linking between two carbon atoms, viz. one carbon atom of the hydrophilic compound and one carbon atom of the substrate.

Such a grafting is necessary for preventing the hydrophilic monomers from passing into solution.

According to one embodiment of the invention, the I.U.D. hydrophilic inclusions contain contraceptive agents: the inclusion of contraceptive products does not give rise to a direct contact between the whole amount of all these products stored and the uterus mucous membrane.

Since the I.U.D. according to the invention comprise inclusions of polymerized hydrophilic substances in which water-soluble contraceptive agents are stored, they show a large advantage over inert I.U.D.'s on which copper-salts or contraceptive products have been sprinkled. Finally, the risk of expulsion from the uterus is restricted, in view of the appropriate shape of the I.U.D. which is not unfavorably modified by the introduction of inclusions into the volume thereof.

The I.U.D. keeps its resilient memory effect so that it resumes its initial shape after having been introduced into the uterus, thus minimizing the risks of an expulsion of the device or of a traumatism.

According to the invention, the I.U.D. is characterized in that the hydrophilic-substance inclusions, in addition to contraceptive agents, contain substances adapted to acclimatize the I.U.D. within the uterus.

According to the invention, the hydrophilic-substances inclusions also contain analgesic substances.

Menometrorrhagias of the I.U.D. are explained by the fragility of the endometrium mucous membrane and the large number of its vessels. Hemorrhages are fostered by the inflammation reaction which is always prevailing. Some treatments were suggested as a remedy to I.U.D. hemorrhages. The substances used in the course of these treatments admit of a better acclimatization of the I.U.D. within the uterus. These substances, according to the invention, are stored in the hydrophilic inclusions of the I.U.D. hydrophobic substrate, and are selected from the group comprising vitamin K, ε-aminocaproic acid, ergotamine, ergotine, diosmine (the latter substance being available on the market under the trade-name "DAFLON"), iron sulphate, ascorbic acid and calcium.

According to the invention, the hydrophobic substrate is a polymerized thermoplastic product such as vinyl acetate, polyethylene or a co-polymer of vinyl acetate and polyethylene, or, more generally, an ethylene co-polymer, a polyether, a polyurethane or a polyacrylonitrile.

It is also possible to use polypropylene, polyamides, polyesters such as ethylen-glycol, polyterephtalate, polyvinyl chloride, polyformaldehyde chloride and polycarbonates or else polytetrafluoroethylene ("Teflon").

According to the invention, the hydrophilic substances is ethylene-glycol acrylate, ethylene-glycol methacrylate, acrylamide, methacrylamide, acrylamide methylol, acrylamide diacetone or an unsaturaded acidic product such as malic acid, acrylic acid, methacrylic acid, fumaric acid, itacomic acid or propylene glycol acrylate or methacrylate.

According to the invention, the contraceptive agents stored in the inclusions are selected from the group comprising copper-, zinc-, cobalt-, lead- and cadmium-salts.

According to the invention, it is possible to add progestational agents such as progesterone, spermicidal agents or oestrogenic soluble agents and products for immunizing from hormones.

These products released by the I.U.D. according to the invention induce a state of transient sterility in the women's body. They are synthetic progestational sexual steroids or oestrogenic compounds. The steroids are selected from the group comprising the derivatives of testosterone, the derivatives of nortestosterone, norethisterone, norethisterone acetate, norethynodrel, ethynodiol diacetate, norgestrienone, norgestrel, chlormadynone acetate, medroxyprogesterone acetate, megestrol acetate, anagestrone acetate and prostaglandine.

The ovulation inhibiting oestrogens used are ethynol oestradiol and mestranol.

According to the invention, antibiotics are introduced into the I.U.D. for the treatment of uteral infections.

According to an embodiment, the I.U.D. comprises a plastic frame, having a great resilient memory, to which is welded a thin sheet at least one of the materials of which the frame and sheet are made being a hydrophobic substance with hydrophilic inclusions, these inclusions being filled with treatment chemical agents and with substances adapted to acclimatize the I.U.D. within the uterus. This embodiment with a thin sheet increases the interface between the I.U.D. and the endometrium, while at the same time spacing the walls, which increases the efficiency about in the same ratio. The shape of the I.U.D. resilient plastic armature can be, for instance, that disclosed in French Pat. No. 1,562,101 of Feb. 5, 1968.

Besides, it was noticed that the polymerization, the grafting and the ionic-radiation-promoted cross-linking of hydrophilic compounds in the hydrophobic substrate according to the method to be described later on, provide the I.U.D. thin sheet with a crumpled structure, thus enhancing its adherence to the uterus wall and decreasing the risk of an expulsion.

According to a variant, the I.U.D. comprises a resilient plastic frame, having a great resilient memory, onto a portion of which are welded two thin sheets, which are, in turn, welded along the peripheries thereof so as to define a free enclosed space between said thin sheets and said frame, at least one of the materials forming the two sheets and the frame being a hydrophobic substance provided with hydrophilic inclusions, these inclusions being filled with treatment chemical agents, with contraceptive products or with substances adapted to acclimatize the I.U.D. within the uterus.

According to another variant, the space defined by the two thin sheets is filled, at least partially, with a solution containing treatment chemical agents (e.g. contraceptive) and substances adapted to acclimatize the I.U.D. in the uterus, these substances and agents being those previously enumerated.

Such a large stock of chemical products permits increases in the time-interval between successive I.U.D.-replacement operations necessitated by the exhaustion of the chemical products contained in the I.U.D.

Inserting substances into the space between the two thin walls ensures the I.U.D. a substantially unlimited life from a chemical standpoint. In such a case, it is absolutely necessary that the two thin sheets forming a portion of the I.U.D. comprise hydrophilic inclusions, in order that the solution containing the treatment and/or contraceptive chemical agents and the acclimatizing agents be in a position to perfuse through the thin wall.

Thin walls with 1/10th-millimeter - thick inclusions perfectly meet that requirement, while at the same time being thin enough for maintaining the requested mechanical resiliency necessary for easily inserting the I.U.D.

Moreover, the crumpling of the two thin sheets due to the introduction their inclusions enhauces the adherence of the I.U.D. in the uterus.

According to the invention, the thin sheet or sheets are welded only along a portion of the plastic frame, which permits to deform the I.U.D. when it is being introduced into the uterus.

According to the invention, the thin sheets welded to the plastic frame are made of a square polymer, viz. a polymer endowed with the same mechanical resistance along two directions at right angles to each other. Such a feature is advantageous in that it limits the risk of tearing the thin sheets welded to the I.U.D. - frame when the I.U.D. is being introduced.

Finally, it was observed that the grafting of vinylic monomers of a hydrophilic nature forming inclusions in the hydrophobic substrate results in a decrease of the I.U.D. surface-hardness due to a resilient effect, since these inclusions overstretch the hydrophobic substrate mesh and enhance the substrate resiliency. This unexpected property is an advantage, since the chafing of the uterus endometrium wall results from the stiffness of the apparatus.

The polymerization of the vinylic monomers for generating inclusions in the volume of the hydrophobic substrate can be carried out by means of ionizing radiations by chemical priming, by means of U.V. radiations, by a previous electrical discharge, by means of ultrasonic waves or simply through raising the substrate temperature.

The I.U.D.'s are, for instance, placed in vinylic monomer aqueous solution, then irradiated after degassing the solution in vacuo. The solution monomers penetrate into the polymerized hydrophobic substrate by spacing apart the meshes and become inflated with water so as to still more distend the polymeric chains, thus permitting the monomer molecules to migrate.

The irradiation polymerizes and grafts these monomers volumetrically so as to generate grafted polymerized inclusions. The polymerized grafted inclusions are cross-linked by means of an ionizing radiation during, or after, the grafting of the hydrophilic monomers.

The thus polymerized and grafted inclusions are fixed within the substrate and no longer diffuse to the outside when the I.U.D. is placed in an aqueous medium. The various substances are introduced into the inclusions by dipping the treated dehydrated I.U.D. provided with inclusions into a solution of suitable agents (treatment contraceptive agents, treatment chemical agents, and acclimatizing agents). These agents in solution perfuse through the hydrophobic substrate so as to be stored in the hydrophilic inclusions. Once the I.U.D. has been withdrawn from these solutions, its inclusions contain the agents and the I.U.D. is ready for use, after having been dried and sterilized. When in contact with the uterus aqueous humors, the I.U.D. desorbs the agents thus filling the inclusions into the uterus.

The desorption velocity of the agents stored in the inclusions varies according to the cross-linking of these inclusions. This cross-linking which determines the size of these inclusions is controlled by submitting the hydrophobic substrate provided with inclusions to a cross-linking of some duration (e.g. by gamma-radiations).

Figure 5:
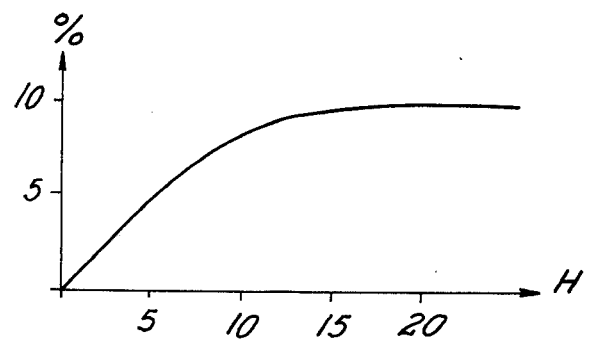
Figure 6:
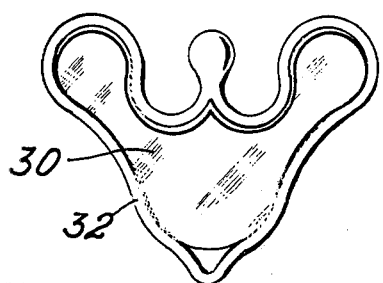
Figure 7:
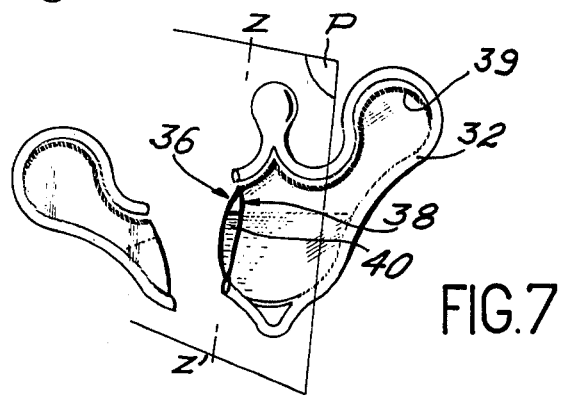

Other features of the invention will appear from the following description given by way of example, with reference to the accompanying drawing, in which:

FIG. 1 is a diagram of the device for grafting and polymerizing inclusions in the hydrophobic substrate forming the I.U.D., FIG. 2 is a diagram of the device for storing the chemical agents for treating and acclimatizing the I.U.D., FIG. 3 shows, in cross-section, a portion of the I.U.D. with inclusions, FIG. 4 is a graph indicating the percentage of ethylene-glycol acrylate, by weight, with respect to the dose (in Mrads) on a polyethylene substrate, at different temperatures, FIG. 5 is a graph indicating the percentage, by weight, of copper stored in the inclusions, FIG. 6 shows an I.U.D. comprising a skin sheet welded to a portion of the frame, and FIG. 7 is an exploded view of an I.U.D. comprising two welded thin sheets, with a chemical-and-acclimatization-agent solution contained in the space defined by the frame and the two thin sheets.

As stated above, the I.U.D. according to the invention improves three basic features of the conventional I.U.D.'s, viz innocuity, efficiency and acceptability.

In FIG. 1 is shown a diagram of the device for grafting and polymerizing inclusions in the hydrophobic substrates which form the I.U.D.'s.

Vessel 2 contains a solution 4 of vinylic monomers 6 in the presence of hydrophobic substrates such as 8. The vessel upper end communicates, through tubing 10 and valve 11, with a pumping device (not shown).

Radiation sources 12, 14 and 16 are gamma sources.

The device according to the invention operates as follows:

hydrophobic substrates such as 8 are placed in solution 4 comprising vinylic monomers which penetrate between the long chains of the hydrophobic polymer. Prior to applying radiations, the solution is degassed by opening valve 11, thus creating a negative pressure above solution 4. Subsequently, the radiation sources are put in operation so as to polymerize the vinylic inclusions within the hydrophobic substrate.

In FIG. 2 is shown vessel 18 containing a hydrophobic substrate provided with hydrophilic inclusions obtained by means of the device of FIG. 1. Solution 20 contains the substances to be perfused through the hydrophobic substrate towards the hydrophilic inclusions. The substances dissolved in 20 are, for instance, contraceptive agents and agents for acclimatizing the I.U.D. in the uterus.

FIG. 3 shows, in cross-section, a portion of the I.U.D.; hydrophobic substrate 24 comprises inclusions of polymerized hydrophilic substance 26. These inclusions contain treatment chemical agents, contraceptive agents or acclimatizing agents, in the solution state or in anhydrous form.

FIG. 4 shows several curves plotting the percentage, by weight, of ethylene-glycol acrylate with respect to the radiation dose (in Mrads), for various solution temperatures. Thus, for instance, for a dose of 1 Mrad, the solution temperature being 60°C, 40%, by weight, of the I.U.D. wall is represented by hydrophilic inclusions, ethylene-glycol acrylate in the present case (the substrate is a co-polymer of ethylene and vinyl acetate).

It can be seen that, if the temperature rises, the vinylic monomer is more easily inserted between the meshes of the network formed by the substrate polymer.

In FIG. 5, the percentage, by weight, of copper stored in inclusions is plotted with respect to the duration of immersion.

The 5000 grams/liter copper-nitrate solution used was at the temperature of 60°C.

FIG. 6 shows an I.U.D. comprising a diaphragm 30 welded to a portion of wall 32 forming the I.U.D. frame.

Of course, the selected specific shape of the I.U.D. is by no means limitative and any other shape likely to permit a fair accommodation of the I.U.D. in the uterus may be used. Wall 30, just like frame 32, is constituted by a hydrophobic substrate comprising hydrophilic inclusions in which have been stored chemical agents and acclimatising agents.

FIG. 7 is an exploded view of an I.U.D. according to the invention, the various portions of which are treated so as to make hydrophilic insertions in which are stored chemical agents in solution and acclimatizing agents. Onto frame 32 of the I.U.D. are welded two thin sheets 36, 38, on either side of that frame. These sheets are welded to each other at 39. Within the thus defined space is stored a solution 40 of chemical agent and of acclimatization agent. In order to show the I.U.D. inside more clearly, the I.U.D. is cut along a plane P passing through straight line ZZ'.

Clinical experiments carried out in vivo on several hundred women for several months have shown that the intra-uterine device according to the invention filled with copper salts was fully accepted by uterus without any shock-promoting side effect, such as expulsion of the device or blood-shed. According to a specific embodiment, the I.U.D. loaded with copper salt releases about 50 µg of copper per day. That release can be regulated, e.g. by modifying the cross-linking of the hydrophilic inclusions.

What is claimed is:

1. An active intra-uterine device comprising a hydrophobic substrate of high mechanical resiliency, wherein said substrate comprises, within the volume thereof, inclusions of polymerized hydrophilic substances grafted on said hydrophobic substrate and cross-linked, in which water-soluble chemical agents have been stored previously, said hydrophobic substrate being porous so that said agents may perfuse through said hydrophobic substrate when the latter is placed in an aqueous medium.

2. A device according to claim 1, wherein the hydrophilic inclusions contain contraceptive agents.

3. A device according to claim 1, wherein the hydrophilic inclusions contain chemical agents selected from the group comprising antibiotics and cortisone.

4. A device according to claim 1, wherein the hydrophilic inclusions contain substances likely to acclimatize the intra-uterine device in the uterus.

5. A device according to claim 1, wherein said hydrophobic substrate is made of an organic polymer selected from the thermoplastic group comprising vinyl acetate, polyethylene, polypropylene, polyamides, ethylene-glycol, polyterephtalate, polyvinyl chloride, polyformaldehyde chloride, polycarbonates, ethylene co-polymers, a polyether, a polyurethane, a polyacrylonitrile and polytetrafluoroethylene.

6. A device according to claim 1, wherein said hydrophobic substrate is an organic co-polymer of vinyl acetate and polyethylene.

7. A device according to claim 1, wherein said hydrophilic substance forming the inclusions is selected from the group comprising ethylene-glycol acrylate, ethylene-glycol methacrylate, acrylamide, methacrylamide, acrylamide methylol, acrylamide diacetone or an unsaturated acidic product such as malic acid, acrylic acid, methacrylic acid, fumaric acid, itaconic acid or propylene glycol acrylate or methacrylate.

8. A device according to claim 2, wherein the contraceptive agents contained in said inclusions are selected from the group comprising copper-, zinc-, cobalt-, lead- and cadmium-salts.

9. A device according to claim 1, wherein said inclusions contain a contraceptive agent selected from the group comprising progestational agents, spermicidal agents and soluble oestrogenic agents.

10. A device according to claim 1, comprising, within said inclusions, substances for acclimatizing the said intra-uterine device within the uterus, wherein said inclusions contain at least one substance selected from the group comprising analgesics, vitamin K, ε-amino caproic acid, ergotamine, diosmine, iron sulphate, calcium and ergotine.

11. A device according to claim 1, including a resilient plastic frame endowed with a high resilient memory, onto a portion of which is welded a thin sheet, at least one of the materials forming said sheet and said frame being made of a hydrophobic substances provided with hydrophilic inclusions, the said inclusions being filled with treatment chemical agents and with substances for acclimatizing the intra-uterine device in the uterus.

12. A device according to claim 1, including a resilient plastic frame endowed with a high resilient memory onto a portion of which are welded two thin sheets which are, in their turn, welded along their peripheries defining an enclosed free space between said thin sheets, at least one of the materials forming the two sheets and the said frame being a hydrophobic substance provided with hydrophilic inclusions, said inclusions being filled with treatment chemical agents and with substances for acclimatizing said intrauterine device within the uterus.

13. A device according to claim 12, wherein said space defined by said two thin sheets is filled with a solution containing contraceptive agents and substances for acclimatizing said intra-uterine device within the uterus.

14. A device according to claim 12, wherein said hydrophobic substrate forming the sheet or sheets welded to the plastic frame is made from a square polymer.

* * * * *